United States Patent
Sweeney, Jr.

[11] Patent Number: 5,763,762
[45] Date of Patent: Jun. 9, 1998

[54] TOTAL DISSOLVED GAS PRESSURE SENSOR, REPLACEABLE COLLECTOR MODULE AND PROCESS

[76] Inventor: John W. Sweeney, Jr., 100 Ogden St., New Haven, Conn. 06511

[21] Appl. No.: 641,555

[22] Filed: May 1, 1996

Related U.S. Application Data

[63] Continuation-in-part of Ser. No. 601,569, Feb. 14, 1996, abandoned, which is a continuation of Ser. No. 819,757, Jan. 13, 1992, abandoned.

[51] Int. Cl.$^6$ ........................................ G01N 7/10
[52] U.S. Cl. ............................ 73/19.05; 73/19.12
[58] Field of Search ................ 73/19.01, 19.1, 73/19.05, 19.06, 19.12

[56] References Cited

U.S. PATENT DOCUMENTS

| | | | |
|---|---|---|---|
| 2,901,327 | 5/1959 | Thayer et al. | 23/230 |
| 2,987,912 | 6/1961 | Jacobson | 73/19 |
| 2,995,922 | 8/1961 | Firth et al. | 73/53 |
| 3,060,723 | 10/1962 | Kapff et al. | 73/19 |
| 3,068,684 | 12/1962 | Axt | 73/19 |
| 3,113,092 | 12/1963 | Dowson et al. | 204/195 |
| 3,150,516 | 9/1964 | Linnebom et al. | 73/19 |
| 3,198,000 | 8/1965 | Schlageter | 204/1 |
| 3,218,242 | 11/1965 | Capuano | 204/1 |
| 3,313,720 | 4/1967 | Robinson | 204/195 |
| 3,319,159 | 5/1967 | Robinson | 324/30 |
| 3,438,241 | 4/1969 | McKinley, Jr. | 73/23 |
| 3,510,406 | 5/1970 | Stack, Jr. | 204/1 |
| 3,764,504 | 10/1973 | Arff et al. | 204/195 |
| 3,849,070 | 11/1974 | Garza et al. | 23/230 |
| 3,871,228 | 3/1975 | Weiss | 73/19 |
| 3,922,904 | 12/1975 | Williams et al. | 73/19 |
| 3,929,008 | 12/1975 | Llewellyn | 73/61 |
| 3,941,566 | 3/1976 | Roche | 23/230 |
| 3,962,046 | 6/1976 | Morrison | 204/1 |
| 3,964,964 | 6/1976 | Dahms | 230/230 |
| 3,997,419 | 12/1976 | Scott et al. | 204/195 |
| 4,058,373 | 11/1977 | Kurz et al. | 55/16 |
| 4,058,447 | 11/1977 | Christiansen | 204/195 |
| 4,207,161 | 6/1980 | Pegnim | 204/195 P |
| 4,208,902 | 6/1980 | Kim et al. | 73/19 |
| 4,222,277 | 9/1980 | Kurtz et al. | 73/721 |
| 4,244,713 | 1/1981 | Goodwin | 45/158 |
| 4,259,165 | 3/1981 | Miyake | 204/1 |
| 4,331,023 | 5/1982 | Allersma et al. | 73/19 |
| 4,461,165 | 7/1984 | Kesson | 73/19 |
| 4,516,580 | 5/1985 | Polanyi | 123/632 |
| 4,542,268 | 9/1985 | Oderheimer | 73/23 |
| 4,563,892 | 1/1986 | D'Aoust | 73/19.05 |
| 4,598,576 | 7/1986 | Goldsmith et al. | 73/19 |
| 4,662,210 | 5/1987 | D'Aoust | 73/19 |
| 4,665,736 | 5/1987 | Yokoyama et al. | 73/19 |
| 5,029,479 | 7/1991 | Bryan | 73/721 |

FOREIGN PATENT DOCUMENTS

| | | | |
|---|---|---|---|
| 5252851 | 3/1982 | Japan | 73/335 |
| 1187013 | 10/1985 | U.S.S.R. | |

Primary Examiner—Michael Brock
Attorney, Agent, or Firm—St. Onge Steward Johnston & Reens LLC

[57] ABSTRACT

An improved total dissolved gas pressure collector has a high ratio of surface area to internal volume and is configured in a compact unit which still permits good fluid flow across it. The module forms part of an improved gas sensor package having high sensitivity (e.g., less than 0.1 mm Hg, preferably less than 0.05 mm Hg) and rapid response times (e.g., less than 5 minutes to 99% of equilibrium, preferably less than 2 minutes to this value). The module comprises: a base having an opening therein; a resilient fitting in said opening in the base; a plurality of upstanding capillary tube supports; an elongated, gas-permeable capillary tube having defined internal volume and defined external surface area, the tube being closed at one end which is secured to one of the supports and having one end adapted to communicate with a total gas pressure transducer through the resilient fitting. Also provided are an acquisition and analysis system including the module, and a method for making the improved module. The devices of the invention are particularly suitable for measuring total dissolved gas pressure in a submarine environment.

20 Claims, 4 Drawing Sheets

TOTAL DISSOLVED GAS PRESSURE SENSOR, REPLACEABLE COLLECTOR MODULE AND PROCESS

RELATED APPLICATIONS

This application is a continuation-in-part of and commonly-assigned U.S. patent application Ser. No. 08/601,569, entitled Saturometer, filed Feb. 14, 1996, by John W. Sweeney, Jr., now abandoned, which in turn is a continuation of and commonly-assigned U.S. patent application Ser. No. 07/819,757 filed Jan. 13, 1992, now abandoned.

TECHNICAL FIELD

The invention provides a replaceable total dissolved gas pressure collector module, a gas sensor package, an acquisition and analysis system including it, and a method for making the improved module and package. The devices of the invention are particularly suitable for measuring total dissolved gas pressure in a submarine environment.

The efficient acquisition and analysis of the total dissolved gas pressure of a fluid is important to industry and for monitoring our natural resources and outside influences on them. There is a need to measure the total pressure of all of the gases dissolved in many types of fluids. Most typically, the need arises for measuring the pressure of atmospheric gases dissolved in bodies of water, such as rivers, lakes, ponds or fish-rearing tanks, to determine changes to enable assurance of proper conditions or at least provide a warning that corrective measures are required. Other applications for this type of monitoring include measuring the dissolved gases in industrial effluents and processing streams, typically in the manufacture of foods, beverages, and pharmaceuticals.

Total dissolved gas pressure monitoring systems are typically based on the use of gas permeable membranes which permit the flow of dissolved gases from a liquid toward a measuring device which can be either electrical or mechanical. Dissolved gases are always trying to come to equilibrium across an interface. Where the interface is a semipermeable membrane, and the liquid is maintained on one side and gases are maintained on the other, measurement of the total dissolved gas pressure is made possible because the gas on the gas side of the membrane always tends to be the same as that on the liquid side.

The practical difficulty that has been addressed, over and over by the prior art, is that total dissolved gas pressure systems will always be subject to physical constraints. It is necessary to provide a membrane with a relatively high surface area to assure a sufficiently large gas transfer to provide energy to actuate the transducer. An opposing consideration is the necessity to maintain relatively low internal volume on the gas side of the membrane, in relation to the surface area of the membrane.

Responsiveness has also been restricted in piezoelectric total dissolved gas pressure transducers because they inherently require relatively large internal spaces on their gas side to provide space for wiring.

While the art has proposed solutions which have enabled modest improvements in sensitivity and responsiveness, the units are not economical because they are still too cumbersome and/or complicated and do not permit field replacement without further reducing the ratio of surface area to internal volume.

There is a present need for total dissolved gas pressure acquisition systems which have high sensitivity and accuracy, but which are more economical due to their initial simplicity and field replaceability. The solution to these interrelated problems is an advance the art is awaiting.

DISCLOSURE OF INVENTION

It is an object of the invention to provide a field-replaceable gas collector module for use in measuring total dissolved gas pressure in a liquid.

It is another object of the invention to eliminate the low sensitivity and response time problems which inhere in prior art designs for total dissolved gas pressure sensor packages.

It is another object of the invention to provide a total dissolved gas pressure module which is compact.

It is another object of the invention to enable easy and reliable assembly of a total dissolved gas pressure collector module.

These and other objects are achieved by the present invention which provides an improved total dissolved gas pressure collector module, a gas sensor package, an acquisition and analysis system including them, and a method for making the improved module.

The total dissolved gas pressure collector module of the invention comprises: a base having an opening therein; a resilient fitting in said opening in said base; a plurality of upstanding capillary tube supports; an elongated, gas-permeable capillary tube having defined internal volume and defined external surface area, said tube being closed at one end which is secured to one of said supports and having one end adapted to communicate with a pressure transducer (e.g., an absolute pressure transducer) through said resilient fitting.

The gas sensor package of the invention will comprise: (a) a gas collection module as defined above, and (b) a total dissolved gas pressure transducer releasably attached to said gas collection module by means of a fitting complementary with said resilient fitting comprised in said gas collection module. Preferably, the total dissolved gas pressure transducer comprises a piezoelectric element having one surface supported in sealed relationship over a vacuum chamber and an opposed surface exposed to a sample chamber open to the total dissolved gas pressure, said sample chamber containing a deformable material to reduce the internal volume of the sample chamber.

The improved method of the invention for making a gas collection module comprises: providing a base having an opening therein; inserting a resilient fitting into said opening in said base; securing a plurality of upstanding capillary tube supports to said base; providing an elongated, gas-permeable capillary tube having defined internal volume and defined external surface area; closing said tube at one end; affixing the closed end to one of said supports and wrapping said tubing about said supports; affixing an open end of said tubing to said resilient fitting to provide means for communication with a total gas pressure transducer through said resilient fitting.

Preferably, at least four upstanding capillary tube supports are provided and said capillary tube is wound about said support to form a pattern of radially and vertically displaced triangular segments. It is also preferred that the resilient fitting comprises a resilient washer, e.g., of rubber, having a base end and an apex end, and said capillary tube is bonded to the resilient fitting at an opening in the apex end. A tapered cavity extends from said base end to said apex end. This cavity is configured to receive a male fitting attached to a pressure transducer.

The ratio of the internal volume to the external surface area are maintained at a low level, e.g., to a reduced ratio which is less than 50%, preferably less than 10%, of that based on the defined values. This can be achieved by utilizing a filler for the membrane, the filler comprising a material selected from the group consisting of thread, monofilament, powder, wire, in situ formed polymer, fluid and a combination of any of these.

BRIEF DESCRIPTION OF THE DRAWINGS

The invention will be better understood and its advantages more apparent from the following detailed description, especially when read in light of the accompanying drawings, wherein.

DETAILED DESCRIPTION OF THE PREFERRED EMBODIMENT

Figure 1:
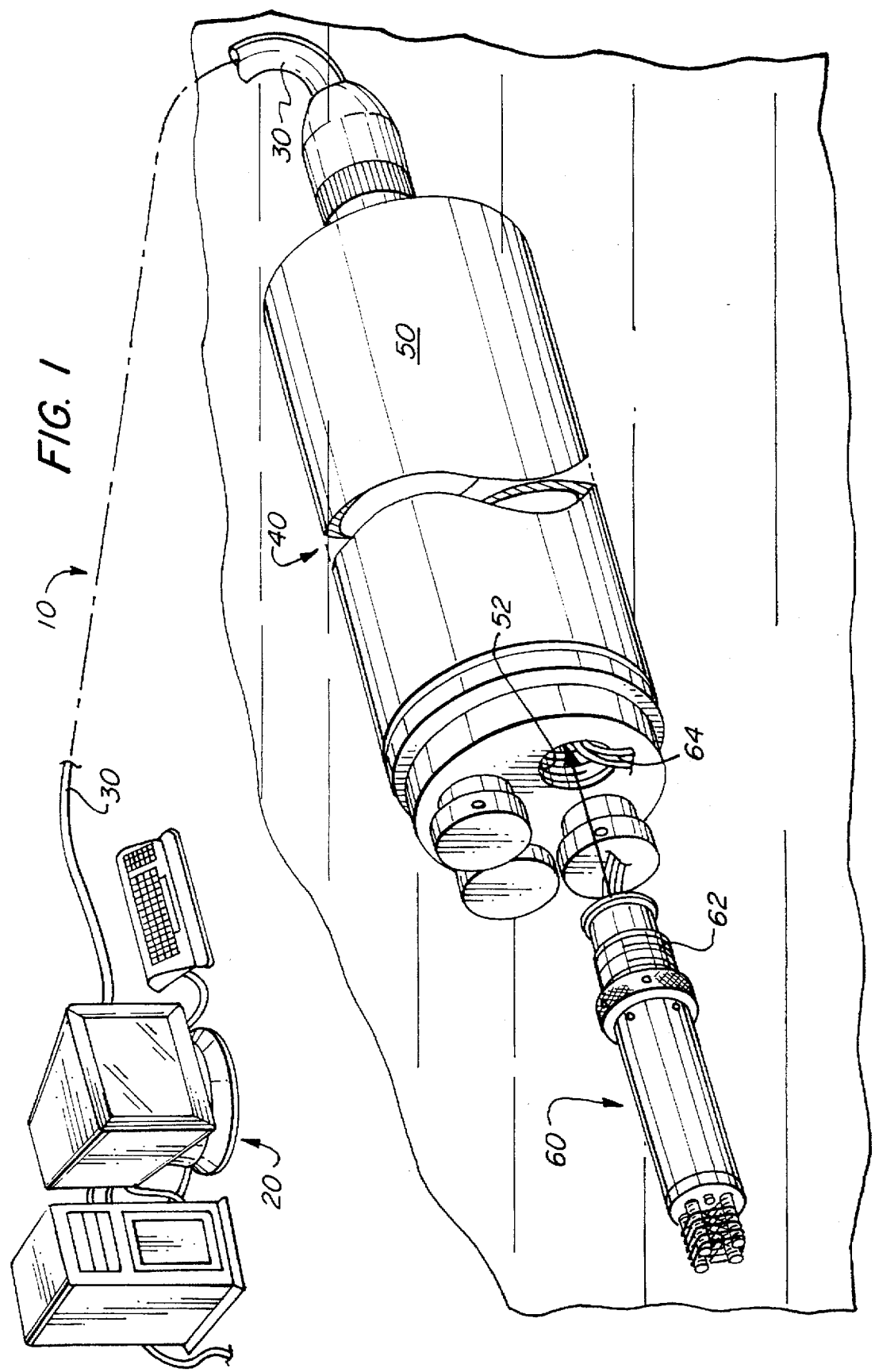
FIG. 1 is a schematic representation of a total dissolved gas pressure acquisition and analysis system of invention.

Reference is made to FIG. 1 which illustrates in schematic form one embodiment of the invention wherein the total dissolved gas pressure of a fluid can be efficiently acquired and analyzed. This system can be used to measure the total pressure of all of the gases dissolved in a fluid. In particular, this system can measure the pressure of atmospheric gases dissolved in bodies of water, such as rivers, lakes, ponds or fish-rearing tanks, to assure proper conditions or at least provide a warning that corrective measures are required. It permits use in other applications as well, such as to measure gases dissolved in industrial effluents and processing streams, typically in the manufacture of foods, beverages, and pharmaceuticals.

In the preferred form of the invention, the improved total dissolved gas pressure collector of the invention has a high ratio of surface area to internal volume and is configured in a compact unit which still permits good fluid flow across it. The module forms part of an improved gas sensor package having high sensitivity (e.g., less than 0.1 mm Hg, preferably less than 0.05 mm Hg) and rapid response times (e.g., less than 5 minutes to 99% of equilibrium, preferably less than 2 minutes to this value).

FIG. 1 is an overall view of a total dissolved gas pressure acquisition and analysis system which has particular applicability for a variety of marine uses. The system, as a unit, is identified generally as 10. Included are a computer terminal 20 which can be of the typical desk top variety in popular use or a special purpose computer dedicated for specific operations. The computer 20 is shown connected by cable 30 to a submergible total dissolved gas pressure data acquisition unit 40.

The data acquisition unit 40 includes a data storage unit 50 for digitally storing data and a gas sensor package 60. In the preferred mode of operation, the data storage unit 50 is housed in a water-tight body and includes electronics and power sources, known in the art, for receiving pressure data from gas sensor package 60 and storing it until called for by computer 20 via connectable cable 30. Typically, the data acquisition unit 40 will be placed within a marine environment, such as at the bottom of, or at a predetermined depth within, a body of water. As practical under the circumstances, the data acquisition unit can be connected to or free from the cable 30. Gas sensor package 60 is shown to have a threaded fitting 62 for mating with a complimentary threaded fitting 52 on the unit 50. A detachable cable 64 is shown, foreshortened, to extend between gas sensor package 60 and the data storage unit 50. Data storage units of this type are known in the art and commercially available, for example from Yellow Springs Instruments as an Endeco/YSI 600XL multi parameter water quality monitoring system running PC6000 software.

Figure 2:
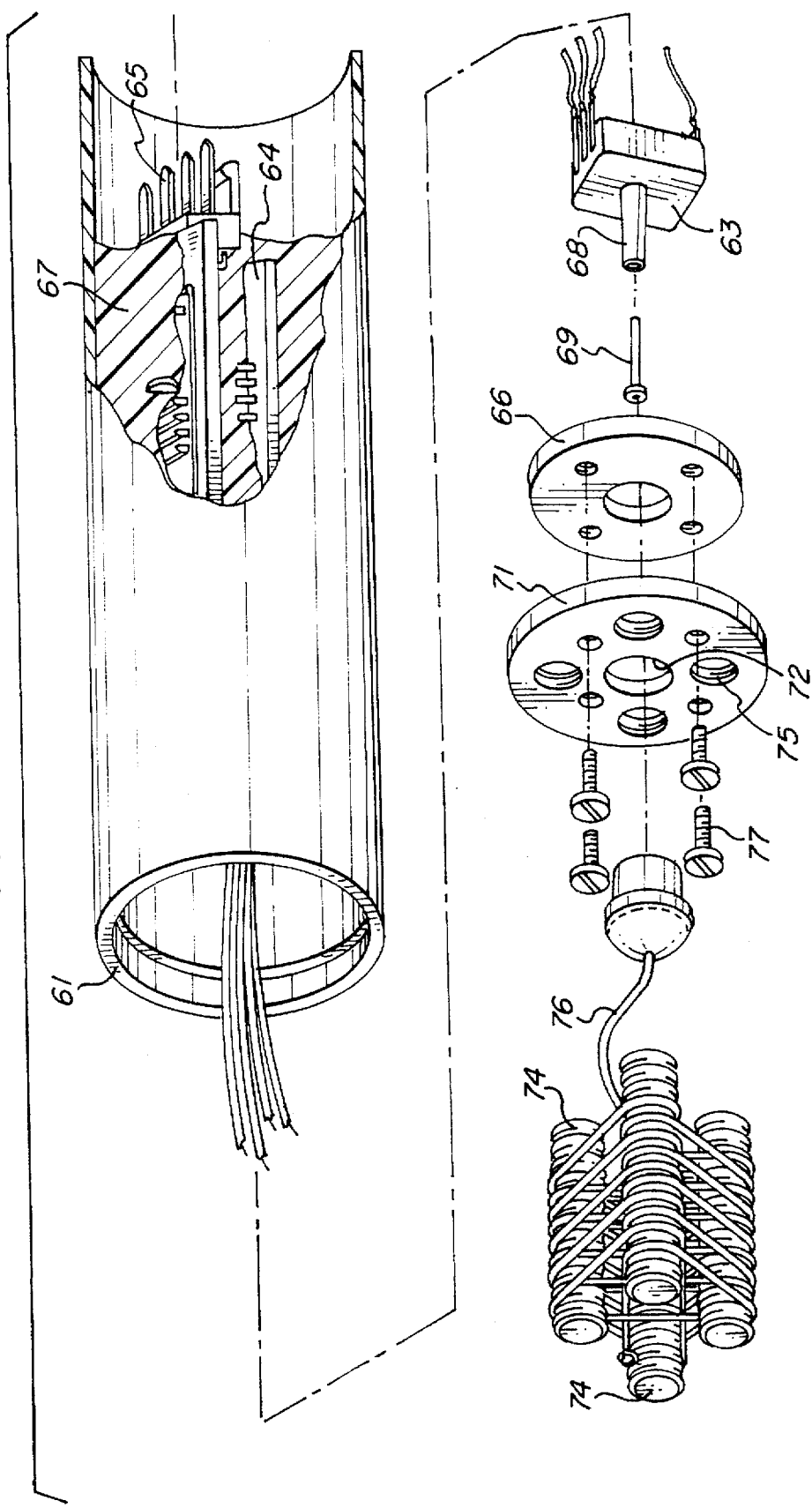
FIG. 2 is a gas sensor package according to invention.

FIG. 2 is an expanded view showing the interrelationship of the parts of the gas sensor package 60. Body 61, shown as tubular, holds pressure transducer 63 and circuitry 64 for processing a signal generated by the transducer which is indicative of total dissolved gas pressure sensed and generating a signal representative of it for transmission to data storage means in unit 50. Typically, this circuitry includes (1) an instrumentation amplifier which buffers and amplifies the signal from the transducer and converts it from a differential to a single ended output, for example a Linear Technology LT 1101 instrumentation amplifier, (2) signal conditioning circuitry to set the offset and slope of the signal, including an LT 1178 dual operational amplifier, (3) an output stage to buffer the conditioned signal, and low-pass filters to screen out noise.

A connector 65 is provided at one end of body 61 for connection to the data storage unit 50. (The mechanical connectors 62 shown in FIG. 1 have been removed for ease of illustration.) The other end of the body 61 is closed by cover plate 66. The interior of body 61 is preferably filled with a suitable potting 67 material, such as a thixotropic urethane. Tapered connector 68 from the transducer 63 extends through cover plate 66 to permit engagement with the total dissolved gas pressure collector module 70 of the invention. As will be explained in connection with FIG. 3, it is preferred to include a metal tube 69 to reduce the dimension of the passage through the connector 68 to the interior of the transducer 63.

Figure 3:
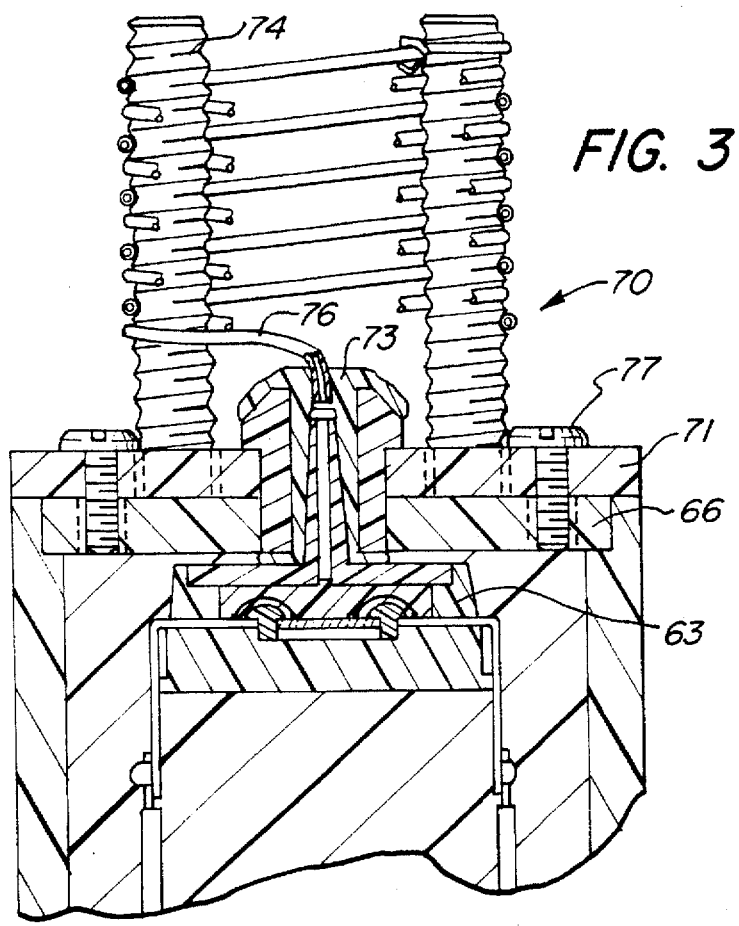
FIG. 3 shows, in cross section, a gas collector module and the preferred manner of attachment to enable field replacement.
Figure 4:
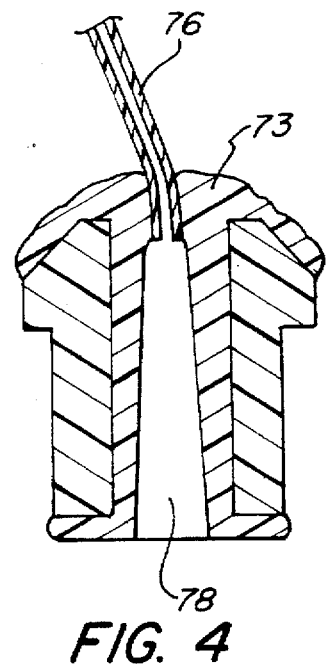
FIG. 4 is a cross sectional view showing the detail of a gasket for coupling the gas collector module to its component gas permeable capillary tube.
Figure 5:
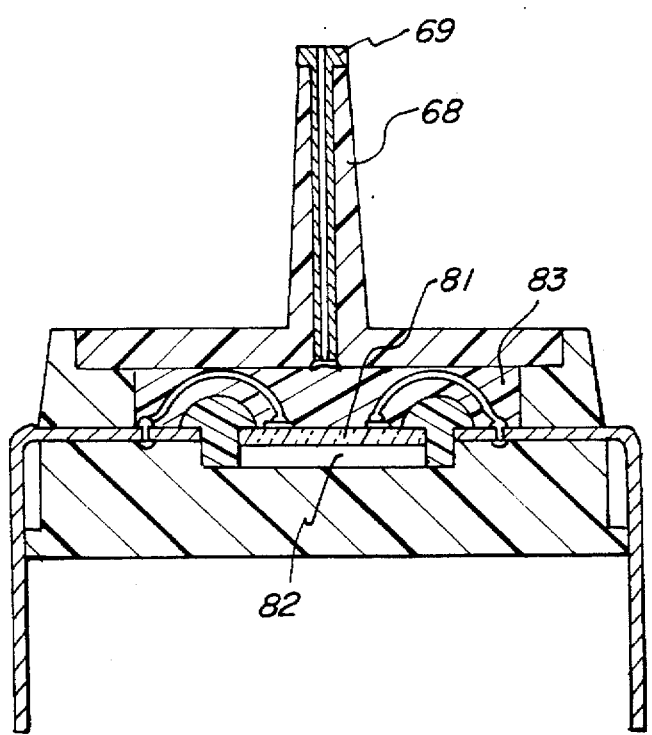
FIG. 5 is a cross sectional view showing the detail of a transducer head for measuring total dissolved gas pressure and means for coupling it to the gas collector module.
Figure 6A:
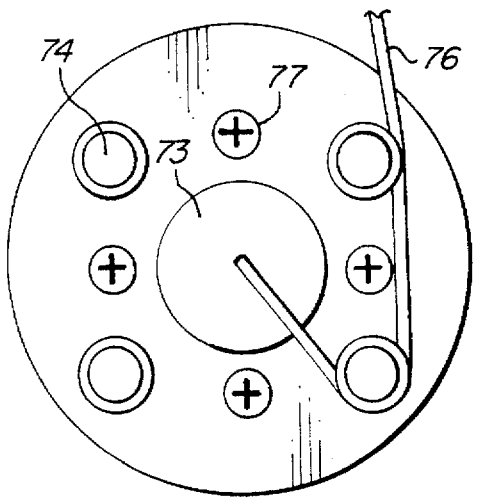
FIGS. 6a–6f show, in sequence, the detail of a preferred winding pattern for the gas permissible capillary tube as shown in FIG. 3.
Figure 6B:
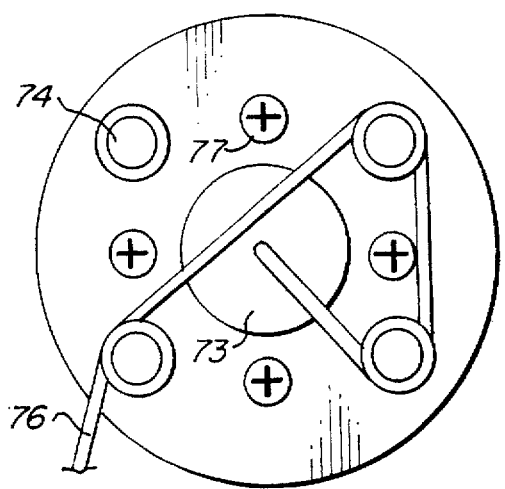
Figure 6C:
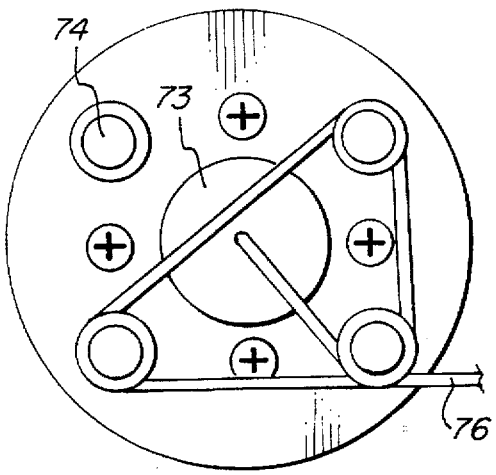
Figure 6D:
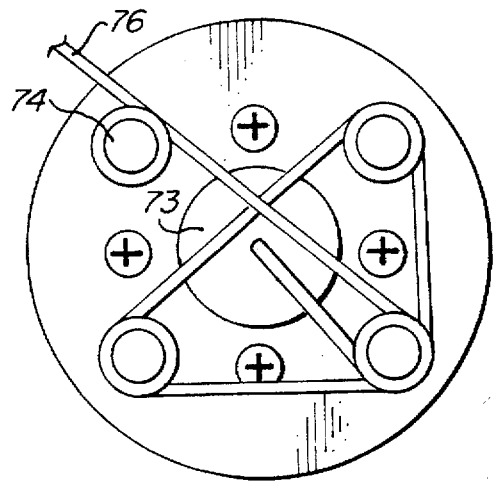
Figure 6E:
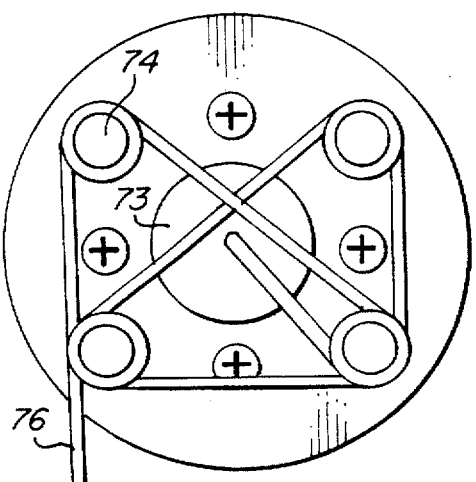
Figure 6F:
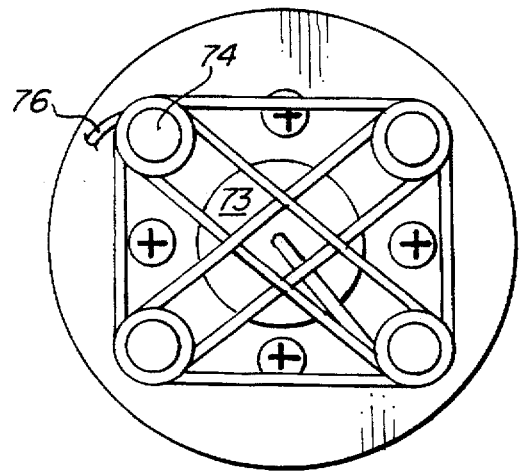

Disk 71 forms the base of the total dissolved gas pressure collector module 70 which can be seen assembled in FIG. 3. Base disk 71 has an opening 72 therein, shown centrally located for permitting communication between the collector module 70 and the transducer 63. A resilient fitting 73 is located in opening 72. A plurality of upstanding capillary tube supports 74 are shown as threaded plastic (e.g., nylon) posts which can be threaded into complementary holes 75 in the base 71. Other means of attachment are also possible, but this means is uniquely effective and simple. An elongated, gas-permeable capillary tube 76 is closed at one end which is secured to one of said supports and has one end open and thereby adapted to communicate with total gas pressure transducer 63 through resilient fitting 73.

Capillary tube 76 is a semipermeable membrane which permits dissolved gases to be separated from a liquid, passing the gas from the liquid though to the interior of the tube. The gas and liquid combination will determine the composition of construction. In the case of separating all dissolved gases from water, a tube made of extruded silicone rubber, having an internal diameter of 0.012 inch and an external diameter of 0.025 inch, is effective. By no means, however, is the invention limited in this regard. For measuring the dissolved gas pressure of a particular gas component, specific polymers will be available.

The total dissolved gas pressure is determined as the gas passes through the membrane under its equilibrium partial pressure. If the volume of gas maintained in the tube is great, it will take a longer time for the pressure within the tube to come to equilibrium with the partial pressure of the gas in the liquid. It is Important to have a high external surface area for the tubular membrane 76 to assure that a good average value for the membrane is achieved. To achieve the best sensitivity and response time, it is necessary to maintain the lowest possible ratio of internal volume to external surface area. The tube has a defined internal volume and a defined external surface area.

The ratio of the internal volume to the external surface area are maintained at a low level, e.g., to a reduced ratio which is less than 50%, preferably less than 10%, of that based on the defined values. This can be achieved by utilizing a filler for the membrane, the filler comprising a material selected from the group consisting of thread, monofilament, powder, wire, in situ formed polymer, fluid and a combination of any of these. Sintered metal and plastic wires and fibers can be suitable filler materials. One preferred filler is a monofilament having a diameter slightly less than the interior diameter of the tube 76. For example, the tube can have an interior diameter of 0.012 inch and the filament can have a diameter of 0.008 inch.

Preferably, at least four upstanding capillary tube supports 74 are provided and the capillary tube 76 is wound about the supports to form a pattern of radially and vertically displaced triangular segments. This can be seen from following the sequence shown in FIGS. 6a through 6f. The winding pattern is unique to this application, providing a series of triangular segments by crossing the tubing around two nonadjacent posts and around two adjacent posts in each course. This pattern provides a dense packing of the tubing while still allowing sufficient open space for the free flow of fluid about and into contact with the tubing. It is an advantage of the invention that the total length of tubing can be decreased by the invention, to a total length of from 0.5 to 3, preferably from 0.75 to 1.5, meters for a tubing having an external diameter of from about 0.020 inch to about 0.030 inch and an inside diameter of from about 0.010 inch to about 0.20 inch. One suitable tubing is available from Sil-Med Corporation as Bio-Sil 30100.

Reference to FIG. 3 shows, in cross section, the detail of the gas collector module 70 and its attachment to base 71 by means of screws 77 which mate with cover plate 66 of the body 61 which holds the transducer 63. FIG. 3 shows a preferred form of resilient fitting 73 which comprises a washer having a base end and an apex end, and said capillary tube is bonded to said resilient fitting at an opening in said apex end. In one embodiment, the resilient fitting comprises a resilient washer, e.g., of rubber, The invention enables good response and sensitivity even when all connections and room for them are on the opposite, sample chamber side. The opposed surface of the element 81 which is exposed to sample chamber 83 is normally open to the total dissolved gas pressure. According to the invention, however, the sample chamber is advantageously filled to the extent possible without overflow to contain a deformable material to reduce the internal volume of the sample chamber. Suitable materials for this purpose are thixotropic polymeric materials, such as urethane epoxy prepolymers, e.g., Insulthane 13-53-4, part A resin, which contains 2% thixotropic agent and is available from Insulcast. The most suitable materials will be thixotropic, but flowable under the conditions of use, or resilient polymeric materials having a softness measured as 10 (Shore A durometer) or less. For thixotropic materials, viscosities at rest should be at least about 1500 cps as measured by a Brookfield RVT viscometer at 25° C. with a number 6 spindle at 12 rpm.

The material used to fill the sample chamber 83 is selected, advantageously, to protect the element 81 from any liquid which may enter due to a break in the system. In the case of water as the fluid, the material should be hydrophobic.

In the industry, absolute pressure transducers are sometimes protected by filling the interior cavity (sample chamber) with silicone oil and sealing the cavity with a stainless steel diaphragm at the opening. That method protects the die and connection from corrosive fluids, but it does not decrease response time and it may make for a stiffer, less-sensitive transducer. It is an advantage of the invention that the transducer is protected without the complexity or change in basic construction which attend the prior approaches.

It is an advantage of the invention that the volume of the channel extending from the capillary tube 76 to the active surface of the transducer is maintained at a very low value. This is facilitated by the capillary tube, the engagement of the male fitting 68 to the resilient fitting 73, the filling of the sample chamber with a material which acts as the active transducer surface by contacting the gas in the sample chamber and transmitting its force exerted by the gas to the transducer, in the manner that hydraulic forces are transmitted. The distance between the end of the tube 76 to the active surface of the transducer is desirably maintained at a value of less than 1 inch, and preferably less than about 0.75 inch.

To assemble the gas collection module of the invention, resilient fitting 73 is inserted into opening 72 in base 71. A plurality of upstanding capillary tube supports 74 are secured to the base. An elongated, gas-permeable capillary tube having defined internal volume and defined external surface area is prepared by closing said tube at one end. The closed end is secured to one of the supports, and the tubing is wrapped about the supports as shown and described. The open end of tubing 76 is then preferably bonded to resilient fitting 73 to provide means for communication with a total gas pressure transducer through said resilient fitting.

In operation, the gas collector module 70 is secured to the cover plate 66 of the body 61 to form an assembled gas sensor package 60. The gas sensor package is then attached to body 50 holding the necessary data storage means to form the total dissolved gas pressure data acquisition unit 40 which can be placed in a river, lake or the like to monitor conditions for a predetermined period of time. The unit 40 is then retrieved, and connected to computer 20 by means of cable 30 to download data for analysis and permanent storage.

The above description is for the purpose of teaching the person of ordinary skill in the art how to practice the present invention, and it is not intended to detail all of those obvious modifications and variations of it which will become apparent to the skilled worker upon reading this description. It is intended, however, that all such obvious modifications and variations be included within the scope of the present invention which is defined by the following claims. The claims cover the indicated components and steps in all arrangements and sequences which are effective to meet the objectives intended for the invention, unless the context specifically indicates the contrary.

I claim:

1. A gas collection module comprising:

a base having an opening therein;

a resilient fitting in said opening in said base;

a plurality of upstanding capillary tube supports;

an elongated, gas-permeable capillary tube having defined internal volume and defined external surface area, said tube being closed at one end which is secured to one of said supports and having one end adapted to directly attach to and communicate with a total gas pressure transducer through said resilient fitting.

2. A gas collection module according to claim 1 wherein at least four upstanding capillary tube supports are provided and said capillary tube is wound about said supports to form a pattern of radially and vertically displaced triangular segments.

3. A gas collection module according to claim 1 wherein said resilient fitting comprises a washer having a base end and an apex end, and said capillary tube is bonded to said resilient fitting at an opening in said apex end.

4. A gas collection module according to claim 1 wherein said resilient fitting comprises a washer having a base end and an apex end, and a tapered cavity extends from said base end to said apex end, said cavity being configured to receive a male fitting attached to a pressure transducer.

5. A gas collection module according to claim 1 wherein said capillary tube contains a filler which decreases the ratio of the internal volume to the external surface area to a reduced ratio which is less than 50% of that based on the defined values.

6. A gas collection module according to claim 5 wherein said reduced ratio is less than 10% of that based on the defined values.

7. A gas collection module according to claim 5 wherein filler comprises mono-filament.

8. A gas collection module comprising:

a base having an opening therein;

a resilient fitting comprising a washer having a tapered channel extending from a base end to an apex end having an opening therethrough;

at least four upstanding capillary tube supports extending outwardly from said base;

an elongated, gas-permeable capillary tube having defined internal volume and defined external surface area, said tube: being closed at one end which is affixed to one of said supports; has another end bonded to said resilient fitting at the opening in said apex end, thereby enabling communication with a total gas pressure transducer through said resilient fitting; and is wound about said support to form a pattern of radially and vertically displaced triangular segments.

9. A gas collection module according to claim 8 wherein said capillary tube contains a filler which decreases the ratio of the internal volume to the external surface area to a reduced ratio which is less than 10% of that based on the defined values.

10. A gas collection module according to claim 9 wherein filler comprises a material selected from the group consisting of thread, mono-filament, powder, wire, in situ formed polymer, fluid and a combination of any of these.

11. A gas sensor package comprising:

(a) a gas collection module including a base having an opening therein;

a resilient fitting in said opening in said base;

a plurality of upstanding capillary tube supports; and an elongated, gas-permeable capillary tube having defined internal volume and defined external surface area, said tube being closed at one end which is affixed to one of said supports and having one end adapted to directly connect to and communicate with a total gas pressure transducer through said resilient fitting; and (b) a total dissolved gas pressure transducer releasably attached to said gas collection module by means of a fitting complementary with said resilient fitting comprised in said gas collection module.

12. A gas sensor package according to claim 11 wherein the total dissolved gas pressure transducer comprises a piezoelectric element having one surface supported in sealed relationship over a vacuum chamber and an opposed surface exposed to a sample chamber open to the total dissolved gas pressure, said sample chamber containing a deformable material to reduce the internal volume of the sample chamber.

13. A gas sensor package according to claim 12 wherein said deformable material comprises a thixotropic polymeric material.

14. A gas sensor package according to claim 12 wherein said deformable material comprises a resilient polymeric material having a softness measured as 10 (Shore A durometer) or less.

15. A gas sensor package according to claim 11 wherein at least four upstanding capillary tube supports extend from said base and said capillary tube is wound about said support to form a pattern of radially and vertically displaced triangular segments.

16. A gas sensor package according to claim 11 wherein said resilient fitting comprises a washer having a base end and an apex end, and a tapered cavity extends from said base end to said apex end, said cavity being configured to receive a male fitting attached to a pressure transducer.

17. A gas sensor package according to claim 11 wherein the capillary tube includes a filler material which reduces the ratio of the internal volume to the external surface area to provide a reduced ratio which is less than 10% of that based on the defined values, and said filler comprises a material selected from the group consisting of thread, mono-filament, powder, wire, in situ formed polymer, fluid and a combination of any of these.

18. A method for making a gas collection module comprising:

providing a base having an opening therein;

inserting a resilient fitting into said opening in said base;

securing a plurality of upstanding capillary tube supports to said base;

providing an elongated, gas-permeable capillary tube having defined internal volume and defined external surface area and adapted to directly attach to and communicate with a total gas pressure transducer through said resilient fitting;

closing said tube at one end;

affixing the closed end to one of said supports and wrapping said tubing about said supports;

affixing an open end of said tubing to said resilient fitting to provide means for communication with the total gas pressure transducer through said resilient fitting.

19. A method for making a gas sensor module according to claim 18 which further includes the step of filling the capillary tube with a material which reduces the ratio of the internal volume to the external surface area to provide a reduced ratio which is less than 10% of that based on the defined values, and said filler comprises a material selected from the group consisting of thread, mono-filament, powder, wire, in situ formed polymer, fluid and a combination of any of these.

20. A method for making a gas sensor module according to claim 18 wherein said resilient fitting comprises a washer having a base end and an apex end, and a tapered cavity extends from said base end to said apex end, said cavity being configured to receive a male fitting attached to a pressure transducer.

* * * * *